US009505685B2

(12) United States Patent
Mertens et al.

(10) Patent No.: US 9,505,685 B2
(45) Date of Patent: Nov. 29, 2016

(54) OLEFIN OLIGOMERIZATION PROCESS

(75) Inventors: Machteld M. W. Mertens, Flemington, NJ (US); Geraldine Tosin, Notre Dame de Gravenchon (FR)

(73) Assignee: ExxonMobil Chemical Patents Inc., Baytown, TX (US)

( * ) Notice: Subject to any disclaimer, the term of this patent is extended or adjusted under 35 U.S.C. 154(b) by 264 days.

(21) Appl. No.: 14/233,205

(22) PCT Filed: Jun. 14, 2012

(86) PCT No.: PCT/EP2012/061369

§ 371 (c)(1), (2), (4) Date: Apr. 7, 2014

(87) PCT Pub. No.: WO2013/013888

PCT Pub. Date: Jan. 31, 2013

(65) Prior Publication Data

US 2015/0038753 A1 Feb. 5, 2015

(30) Foreign Application Priority Data

Jul. 25, 2011 (EP) .................................... 11175237

(51) Int. Cl.

| | |
|---|---|
| ***C07C 2/02*** | (2006.01) |
| ***C07C 7/12*** | (2006.01) |
| ***B01J 20/06*** | (2006.01) |
| ***B01J 20/08*** | (2006.01) |
| ***B01J 20/28*** | (2006.01) |
| ***B01J 21/04*** | (2006.01) |
| ***C07C 2/12*** | (2006.01) |
| ***C07C 2/10*** | (2006.01) |
| ***C07C 2/18*** | (2006.01) |
| ***C07C 2/30*** | (2006.01) |
| ***B01J 21/06*** | (2006.01) |
| ***B01J 23/14*** | (2006.01) |
| ***B01J 23/30*** | (2006.01) |
| ***B01J 23/745*** | (2006.01) |
| ***B01J 35/00*** | (2006.01) |
| ***B01J 35/02*** | (2006.01) |
| ***B01J 35/10*** | (2006.01) |
| ***B01J 37/00*** | (2006.01) |
| ***B82Y 30/00*** | (2011.01) |

(52) U.S. Cl.

CPC .................. *C07C 7/12* (2013.01); *B01J 20/06* (2013.01); *B01J 20/08* (2013.01); *B01J 20/28007* (2013.01); *B01J 20/28057* (2013.01); *B01J 20/28061* (2013.01); *B01J 21/04* (2013.01); *B01J 21/063* (2013.01); *B01J 21/066* (2013.01); *B01J 23/14* (2013.01); *B01J 23/30* (2013.01); *B01J 23/745* (2013.01); *B01J 35/0013* (2013.01); *B01J 35/026* (2013.01); *B01J 35/1019* (2013.01); *B01J 37/0009* (2013.01); *B01J 37/009* (2013.01); *B01J 37/0036* (2013.01); *B82Y 30/00* (2013.01); *C07C 2/10* (2013.01); *C07C 2/12* (2013.01); *C07C 2/18* (2013.01); *C07C 2/30* (2013.01); *B01J 2220/42* (2013.01); *B01J 2220/56* (2013.01); *C07C 2521/04* (2013.01); *C07C 2521/08* (2013.01); *C07C 2521/12* (2013.01); *C07C 2523/20* (2013.01); *C07C 2523/755* (2013.01); *C07C 2527/10* (2013.01); *C07C 2527/12* (2013.01); *C07C 2527/173* (2013.01); *C07C 2527/18* (2013.01); *C07C 2529/40* (2013.01); *C07C 2529/65* (2013.01); *C07C 2529/70* (2013.01); *C07C 2529/85* (2013.01); *C07C 2529/89* (2013.01); *C07C 2531/04* (2013.01); *C07C 2531/14* (2013.01); *Y02P 20/52* (2015.11)

(58) Field of Classification Search

CPC ........................................................ C07C 7/12
USPC ........ 585/823, 820, 833; 208/228, 203, 229, 208/236
See application file for complete search history.

(56) References Cited

U.S. PATENT DOCUMENTS

| | | | |
|---|---|---|---|
| 4,973,790 A | 11/1990 | Beech, Jr. et al. | |
| 5,177,282 A | 1/1993 | Nierlich et al. | |
| 5,414,183 A | 5/1995 | Abrevaya et al. | |
| 7,154,014 B1 | 12/2006 | Negiz et al. | |
| 2002/0111523 A1 | 8/2002 | Mathys et al. | |
| 2005/0137442 A1 | 6/2005 | Gajda et al. | |
| 2007/0086933 A1 | 4/2007 | Negiz et al. | |
| 2007/0213575 A1* | 9/2007 | Godsmark ................ | C07C 2/12 585/518 |
| 2008/0194903 A1* | 8/2008 | Schubert ................. | C07B 37/08 585/823 |

FOREIGN PATENT DOCUMENTS

| | | |
|---|---|---|
| WO | WO 02/060842 | 8/2002 |
| WO | WO 2004/014546 | 2/2004 |
| WO | WO 2006/089957 | 8/2006 |

OTHER PUBLICATIONS

Tijburg et al. "Sintering of Pseudo-boehmite and gamma alumina" Journal of Materials Science 26 (1991) pp. 5945-5949.*

(Continued)

*Primary Examiner* — Sharon Pregler
(74) *Attorney, Agent, or Firm* — Darryl M. Tyus

(57) ABSTRACT

The invention provides an olefin oligomerization process comprising the steps of: i) reducing the level of nitriles in an olefin feed by contacting the feed with a guard bed comprising gamma alumina having a surface area greater than 250 $m^2/g$; and ii) contacting the olefin feed obtained in step i) with an oligomerization catalyst under conditions suitable to oligomerize the olefins in the feed; wherein the gamma alumina used in step i) has been obtained from needle shaped boehmite.

8 Claims, No Drawings

(56) References Cited

OTHER PUBLICATIONS

Paglia et al., "*Boehmite-Derived γ-Alumina System. 2. Consideration of Hydrogen and Surface Effects*", Chemistry of Materials, vol. 16, No. 10, May 1, 2004, pp. 1914-1923.

Stepanov et al., "*Interaction of Acetonitrile with Olefins and Alcohols in Zeolite H-ZSM-5: In Situ Solid-State NMR Characterization of the Reaction Products*", Chem. Eur. J. 1997, vol. 3, Issue 1, pp. 47-56.

Wilson et al., "*Energetics of formation of lamellar porous microstructures in* γ-$Al_2O_3$", Journal of Materials Science, Springer, Netherlands, NL, vol. 15, No. 12, Jan. 1, 1980, pp. 3081-3089.

Wilson et al., "*The Porosity of Aluminum Oxide Phases Derived from Well-Crystallized Boehmite: Correlated Electron Microscope, Adsorption, and Porosimetry Studies*", Journal of Colloid and Interface Science, Academic Press, New York, NY, US, vol. 82, No. 2, Jan. 1, 1981, pp. 507-517, 1980.

Wilson et al., "*Phase transformations and development of microstructure in boehmite-derived transition aluminas*", British Ceramic Society Proceedings, Maney Publishing, GB, vol. 28, Jan. 1, 1979, pp. 281-294, 1981.

Yang, R. T., "*6.7. Activated Alumina as Special Sorbents*," Chapter 6, Silica Gel, MCM, and Activated Alumina, Adsorbents: Fundamentals and Applications, John Wiley & Sons, Inc., pp. 131-156, 2003.

* cited by examiner

OLEFIN OLIGOMERIZATION PROCESS

CROSS REFERENCE TO RELATED APPLICATIONS

This application is a National Stage Application of International Application No. PCT/EP2012/061369, filed Jun. 14, 2012, the disclosure of which is incorporated by reference in its entirety.

FIELD OF INVENTION

The present invention relates to an oligomerization process and a guard bed suitable for the oligomerization process.

BACKGROUND OF THE INVENTION

The higher olefins oligomerization process converts light olefins, typically, $C_3$ to $C_6$ light olefins, to oligomers (higher olefins), typically such as octenes, nonenes and dodecenes. These higher olefins are then used in the production of various products such as plasticizers and solvents. The feedstocks used for the higher olefins oligomerization process come from various sources, such as catalytic crackers and steam crackers. Such feeds are known to contain nitrogen containing compounds, which act as poisons for the catalysts typically used in the higher olefins oligomerization process. The presence of poisons in the feeds has a significant impact on the catalyst life, and thus on the operation and economics of the higher olefins oligomerization process. It is known that acidic catalysts like solid phosphoric acid or zeolites typically used in olefin oligomerization processes are susceptible to poisoning from trace amounts of sulphur-, nitrogen- and oxygen-containing compounds in the feed. Such poisons adsorb on the acidic catalysts, blocking acid sites and pores. This causes enhanced deactivation of the catalyst and shorter catalyst life. Special precautions and feed cleanup is required in case the poison levels are too high.

At present there is no known single process that can quantitatively remove all nitrogen poisons from olefin feeds useful in the higher olefins oligomerization process to meet required feed quality specifications. Water washing only partially removes nitriles, such as acetonitrile, from certain olefin feeds. Not only is the removal process difficult but it is expensive and generates a lot of waste water.

The interaction of acetonitrile with olefins and alcohols in zeolite H-ZSM-5 is described in Chem. Eur. J. 1997, 3, No. 1 pages 47 to 56 "Interaction of Acetonitrile with Olefins and Alcohols in Zeolite H-ZSM-5: In-Situ Solid-State NMR Characterization of the Reaction Products" Alexander G. Stepanov and Mikhail v. Luzgin.

U.S. Pat. No. 4,973,790 discloses a process for oligomerizing $C_2$ to $C_{10}$ olefins obtained by catalytic cracking of heavy crude oil. Feed pretreatment is practised to remove basic nitrogen compounds present in the light olefin feed with a water wash or guard bed. Where the pretreatment comprises at least two steps, the first step is either a water wash step or contact of feed with a solid bed having an affinity for basic nitrogen. The second step is contact with a zeolitic bed. Only use of a conventional resin guard bed is exemplified. No specific nitrogen compounds are mentioned.

U.S. Pat. No. 5,414,183 discloses isomerization and etherification reactions. Nitrogen contaminants in the hydrocarbon feed stream are converted to hydrolysis products by contact with an alkaline solution. Residual products in the hydrocarbon phase may be removed by a variety of known means including water washing, stripping and adsorption.

US 2005/0137442 relates to a transalkylation process where organic nitrogen compounds, including acetonitrile and propionitrile, are removed from an aromatic feed stream by contacting the stream with an acidic molecular sieve at a temperature of at least 120° C.

US2007/0086933 discloses a translakylation process for reacting carbon number nine aromatics with toluene to form carbon number eight aromatics such a para-xylene. The process uses a guard bed of gamma aluminium oxide made from boehmite crystals, prior to contacting with a translakylation catalyst in order to remove chlorides from the aromatic feed.

WO2004/014546 teaches a guard bed made of finely divided lead oxide and a particulate support material, such as aluminium oxide. This guard bed can be used to remove chlorides present in a process gas stream containing carbon monoxide and steam, before contact with a copper containing catalyst.

SUMMARY OF THE INVENTION

The present invention provides an olefin oligomerization process comprising the steps of:

i) reducing the level of nitriles in an olefin feed by contacting the feed with a guard bed comprising gamma alumina having a surface area greater than 250 $m^2/g$; and ii) contacting the olefin feed obtained in step i) with an oligomerization catalyst under conditions suitable to oligomerize the olefins in the feed; wherein the gamma alumina used in step i) has been obtained from needle shaped boehmite.

Preferably the largest dimension of the needle shaped boehmite is 3 nm or less.

Optionally, the guard bed may comprise at least another metal oxide besides gamma alumina. Conveniently, this other metal oxide may be selected from tin oxide, zirconium oxide, titanium oxide, iron oxide, tungsten oxide and alumina of any phase other than gamma alumina.

Preferably the nitriles present in the olefin feed are selected from acetonitrile, propionitrile and mixtures thereof.

Convenient oligomerization catalyst that may be used in step (ii) include zeolites, nickel oxide, phosphoric acid, mixtures or combinations thereof.

In an embodiment, the guard bed used in step i) and the oligomerization catalyst used in step ii) are in separate vessels.

In a preferred embodiment, the temperature employed during process step i) is in the range of 150 to 250° C.

In another preferred embodiment, the olefin is selected from olefins having 3 to 6 carbon atoms, preferably from 3 to 5 carbon atoms.

The present invention further provides the use of gamma alumina obtained from needle shaped boehmite for reducing the content of nitriles in an olefin feed intended for use in an oligomerization process.

DETAILED DESCRIPTION

Olefin Feed

The present invention provides a process for oligomerizing an olefin feed, which uses a step of reducing the level of nitriles in the olefin feed, before the olefin feed is subjected to oligomerization. As used herein, "olefins" refers to any unsaturated hydrocarbons having the formula $C_nH_{2n}$, wherein C is a carbon atom, H is a hydrogen atom, and n is the number of carbon atoms in the olefin. According to this invention, the olefins in the feed typically have from 2 to 15 carbon atoms, such as at least 3 and no more than 8 carbon atoms, and typically at least 3 and no more than 6 carbon atoms. The olefins present in the feed may also be referred to as lower olefins or light olefins.

The feed may also comprise one or more paraffins. As used herein, "paraffins" refers to any of the saturated hydrocarbons having the formula $C_nH_{2n+2}$, wherein C is a carbon atom, H is a hydrogen atom, and n is the number of carbon atoms in the paraffin. The paraffins that may be present in the olefin feed typically have from 1 to 25 carbon atoms, such as from 1 to 15 carbon atoms, and conveniently at least 3 and no more than 6 carbon atoms. Examples of suitable paraffins include methane, ethane, propane, butane, pentane, hexane, isomers thereof and mixtures thereof. If present in the feed, the paraffins may have the same or a different number of carbon atoms as the olefins.

If present, the paraffin acts as a diluent. If used, the olefin feed may comprise at least 10%, at least 25%, at least 30%, at least 35%, or at least 40% paraffin, based upon the total volume of the feed. Alternatively stated, if used, the diluent may be present in the olefin feed in the range from 10% to 40%, alternatively, from 10% to 35%, and alternatively, from 20% to 35% based upon the total volume of the feed. The diluent may also be fed to the reactor(s) separately from the olefin feed. When fed separately, the diluent may be fed in amounts equivalent to those mentioned above, where the diluent is co-fed with the feed. These amounts may not necessarily be the same as the ranges stated above given that more or less of the diluent may be necessary when fed separately to provide an equivalent.

In a class of embodiments, the olefin feed comprises olefins selected from propene, butenes, pentenes, hexenes, their isomers, and mixtures thereof. The process of this invention is especially useful for the oligomerization of feeds comprising propene, butenes, pentenes, their isomers, and mixtures thereof. As used herein, "isomers" refers to compounds having the same molecular formula but different structural formula.

Additionally, the feed may comprise an oligomer (higher olefin), for example, a dimer, such as one provided by recycling a part of an olefin oligomerization product stream. As used herein, "oligomer(s)" or "oligomer product" refers to an olefin (or a mixture of olefins) made from a few light olefins. For example, oligomers include dimers, trimers, tetramers, obtained from two, three or four light olefins of the same number of carbon atoms, mixed oligomers, obtained from 2 or more olefins having different numbers of carbon atoms and mixtures thereof. In a class of embodiments, "oligomer(s)" refers to an olefin (or a mixture of olefins) having 20 carbon atoms or less, alternatively, 15 carbon atoms or less, such as 10 carbon atoms or less, alternatively, 9 carbon atoms or less, and conveniently, 8 carbon atoms or less, that has been obtained by linking two or more light olefins together. As used herein, "oligomerization process" refers to any process by which light olefins are linked together to form the oligomer(s) as defined above. As used herein, the term "oligomerization conditions" refers to any and all those variations of equipment, conditions (e.g. temperatures, pressures, weight hourly space velocities etc.), materials, and reactor schemes that are suitable to conduct the oligomerization process to produce the oligomer(s) as known and applied in the art and discussed more below.

In a class of embodiments, the feed comprises 30 wt % or more olefins, such as 40 wt % or more olefins, alternatively, 50 wt % or more olefins, alternatively, 60 wt % or more olefins, alternatively, 70 wt % or more olefins, and alternatively, 80 wt % or more olefins, based upon the total weight of the olefin feed.

In any of the embodiments described herein, the feed should be totally free, or at least substantially free, of aromatic hydrocarbon compounds that consist solely of hydrogen and carbon atoms. In this context, "substantially free" means that the olefin feed contains 25 wt % or less, preferably 15 wt % or less, more preferably 10 wt % or less, such as 5 wt % or less, and most preferably 1 wt % or less aromatic hydrocarbon, based upon the total weight of the olefin feed.

Examples of suitable olefin feeds include untreated refinery streams such as Fluidized Catalytic Cracking (FCC) streams, coke streams, pyrolysis gasoline streams or reformates.

Other examples of suitable olefin feeds include refinery feeds often referred to as Raffinate-1 (RAF-1), Raffinate-2 (RAF-2) or Raffinate-3 (RAF-3). Typically, Raffinate-1, Raffinate-2 and Raffinate-3 may be regarded as streams obtainable at various stages in the processing of crude $C_4$ streams obtained from petroleum refining processes. These streams are usually from olefin steam crackers but may also come from refinery catalytic crackers, in which case they generally contain the same components but in different proportions. The first stage of processing these crude $C_4$ refinery streams is to remove butadiene from these streams, such as by solvent extraction or hydrogenation. Butadiene is generally present in the crude $C_4$ refinery streams as 40-45 wt. % of the stream. The product obtained after butadiene removal is Raffinate-1. It generally consists of isobutylene, the two isomers of n-butane, 1-butene and 2-butene, and smaller quantities of butanes and other compounds. The next step consists in removing isobutylene, usually by reaction of isobutylene with methanol to produce methyl-tert-butylether (MTBE), which then produces Raffinate-2. Raffinate-3 (RAF-3) is less common but may be obtained after separation of 1-butene from Raffinate-2. Raffinate-3 typically has a residual 1-butene content of about 1%.

In another embodiment, the feed comprises an FCC light olefin stream that typically comprises ethane, ethylene, propane, propylene, isobutane, n-butane, butenes, pentanes, and other optional components.

Optionally, the olefin feed may also be hydrated (i.e., contacted with water) prior to oligomerization. In an embodiment, sufficient water is used to saturate the feed. In particular, the feed may comprise from about 0.01 to about 0.25, alternatively, from about 0.02 to about 0.20, and alternatively, from about 0.03 to about 0.10, mol % water based on the total hydrocarbon content of the feed. If desired and by way of example, the water content of the feed may be increased by passage through a thermostatted water saturator. The olefin feed used in the oligomerization step can therefore be wet or dry.

According to the present invention, any of the above-described olefin feeds contains organic nitrile contaminants which must be removed to an acceptable level before the olefins undergo oligomerization. As used herein, "nitrile" is any organic compound that has a nitrile group (or —C≡N functional group). In the nitrile group, the carbon atom and the nitrogen atom are triple bonded together. As used herein, "acetonitrile" (ACN) is the chemical compound with formula $CH_3CN$. This colorless liquid is the simplest organic nitrile. As used herein, "propanenitrile", "propionitrile", or "ethyl cyanide" is a nitrile with the molecular formula $C_2H_5CN$ and the terms may be used interchangeably. It is also clear liquid. As used herein, "nitrile" may also refer to heavier nitriles. In the most preferred embodiment the nitrile to be removed is any of acetonitrile and propionitrile. These compounds are especially toxic to oligomerization catalysts and their removal leads to significant catalyst life improvement.

Typically, the nitrile content in the olefin feed upstream of the guard bed may be about 3 ppm or more, such as about 5 ppm or more, typically, 10 ppm or more, such as 20 ppm or more, and yet alternatively, 30 ppm or more, calculated on a nitrogen atom basis by weight (wt ppm), with respect to the total weight of hydrocarbon in the olefin stream.

Guard Bed and Nitrile Removal Process

The present invention provides a process for oligomerizing an olefin feed, which uses a step of reducing the level of nitriles in the olefin feed, before the olefin feed is subjected to oligomerization. This step of reducing the level of nitriles in the olefin feed is accomplished by contacting the olefin feed with gamma alumina. Contacting is typically done by flowing the olefin feed through a bed of gamma alumina, thereby allowing nitriles to be adsorbed on gamma alumina. Such a bed of gamma alumina therefore acts as a guard bed, that is, it reduces the level of nitriles present in the olefin to levels where nitriles will no longer interfere in the subsequent olefin oligomerization step. At the same time, the guard bed avoids oligomerization or any other reactions which might compete with the guard bed's role of adsorbing nitriles from the olefin feed.

The guard bed of the present invention comprises gamma alumina, preferably obtained from needle shaped boehmite By needle shaped it is meant that the boehmite is in the form of crystals which are substantially rod shaped having tapering ends and where the mean average ratio Z/Y of length (Z) to diameter measured at the thickest part of the needle (Y) is at least 2.5. Each needle may be made up of smaller crystals agglomerated together. The shape and the size of the Boehmite crystals can be determined by microscopy, such as Scanning Electron Microscopy (SEM) or Transmission Electron Microscopy (TEM).

The transformation of boehmite into gamma alumina is described in Adsorbents: Fundamentals and applications by Yang, Ralph T., Wiley-Interscience, 2003, Chapter 6 or in Catalyst Supports and Supported Catalyst by A. B. Stiles (Ed.), Butterworth-Heinemanm, 1987, Chapter 2. It is typically carried by submitting boehmite to a treatment at elevated temperature for a period of several hours. Gamma alumina of particular interest in the context of the present invention can be obtained from small sized (i.e. less than 4 nm) needle shape boehmite, which has been submitted to temperatures of 500° C., preferably at least 520° C., conveniently 540° C., for several hours, until the conversion of boehmite to gamma alumina is complete. This results in gamma alumina of small crystallite sizes and with high surface area, as determined by BET Nitrogen adsorption techniques. Conveniently, gamma alumina's used as guard materials according to the present invention have a BET nitrogen surface area of at least 200 $m^2/g$, such as at least 220 $m^2/g$, or even at least 250 $m^2/g$. We have found that when boehmite is treated at a temperature with higher than 600° C. boehmite converts to gamma alumina with a surface area that is lower than if treated at temperatures lower than 600° C. It is thus preferred that boehmite be thermally treated at a temperature lower than 600° C., even preferably lower than 580° C.

The present inventors have found that gamma-alumina having the above-mentioned properties, when employed in a non-zeolitic guard bed, is most effective at adsorbing acetonitrile from a contaminated olefin feed intended for use in an olefin oligomerization process.

Besides gamma alumina, the guard bed of the present invention may comprise one or more additional metal oxides. The additional metal oxides are not especially limited and may be selected from tin oxide, zirconium oxide, titanium oxide, iron oxide, magnesium and tungsten oxide, silicon oxide, copper oxide, nickel oxide, zinc oxide, alumina's of other forms than gamma alumina and mixtures thereof.

There are different ways to prepare multi metal oxide compositions, including physical mixing and co-precipitation methods. The metal oxide(s) used in the guard bed may also contain metals and noble metals added to the metal oxide or multi metal oxide by impregnation or other preparation methods.

The olefin feed can be contacted with the guard bed at temperatures from about 50° C. to about 350° C., preferably from about 50° C. to 320° C. In one embodiment, the preferred temperature range is from about 100° C. to about 300° C., alternatively, from about 150° C. to about 250° C., and alternatively, from about 200° C. to about 250° C. However, if the step of removing basic organic nitrogen from the olefin feed is carried out in a reaction vessel that is separate from the oligomerization reactor, lower temperatures can prove suitable too, such as from about 50° C. to below about 100° C. The pressure may be in the range of from about 400 psig to about 4000 psig (2860 kPa to 27688 kPa), and preferably, from about 500 psig to about 1500 psig (3550 kPa to 10446 kPa). The olefin weight hourly space velocity may be in the range of from about 0.1 $hr^{-1}$ to about 20 $hr^{-1}$ or from about 0.5 $hr^{-1}$ to about 5 $hr^{-1}$. In one embodiment, the process is conducted at a temperature of 80-350° C., an olefin weight hourly space velocity of 0.1-20 $hr^{-1}$, and a pressure of 2860-27688 kPa. In another embodiment, the process is conducted at a temperature of 130-320° C., an olefin weight hourly space velocity of 0.5-5 $hr^{-1}$ and a pressure of 3550-10446 kPa.

The gamma alumina used as the guard bed can be placed in the same vessel as the vessel in which olefin oligomerization takes place or it can be in separate vessels. Whether in the same or different vessels the guard bed is placed upstream of the olefin oligomerization catalyst. The benefit of the olefin oligomerization catalyst and guard bed being in separate vessels is that there can be independent control of process conditions such as temperature and pressure to ensure optimal rates for both steps. The benefit of the catalyst and guard bed being in the same vessel is that the arrangement for the oligomerization process is more compact and easier to construct. More than one guard bed having the same or different composition can be used. The presence of more than one guard bed enables a longer run length. Also, while one or more guard beds are in use, the other(s) can be regenerated. This ensures a continuous process for the removal of basic organic nitrogen and purification of the olefin feed.

After contacting with the guard bed, the basic organic nitrogen content in the olefin stream downstream of the guard bed is about 1.50 ppm or less, alternatively, 1.00 ppm or less, such as 0.50 ppm or less, alternatively, 0.30 ppm or less, 0.20 ppm or less, and yet preferably 0.10 ppm or less calculated on a nitrogen atomic basis by weight (wt ppm) relative to the total weight of hydrocarbons in the olefin stream.

Oligomerization

Once the level of nitriles in the feed has been decreased to suitable levels, the olefin feed is contacted with a catalyst under conditions suitable to form higher olefins through oligomerization.

One or more catalysts may be used for the oligomerization. Any catalyst suitable for olefin oligomerization, whether homogeneous or heterogeneous, may be used, Heterogeneous catalysts may be crystalline or amorphous (non-crystalline) catalysts. Crystalline catalysts include without limitation molecular sieve catalysts such as, for example, zeolite catalysts, in particular, H-zeolites (i.e. zeolites in their proton or acidic form).

Non-crystalline heterogeneous catalysts include without limitation solid acid catalysts such as, for example, solid phosphoric acid (SPA) catalysts and supported metal catalysts or supported metal oxide catalysts. Non-limiting examples of olefin oligomerization processes using such catalysts may be found as follows. Olefin oligomerization using SPA catalysts is disclosed for example in U.S. Pat. No. 6,025,533, WO 92/13818 or WO 2005/058777. The CATPOLY™ Process (UOP and Sud Chemie) employs phosphoric acid on a silica support. The OCTOL™ Process (UOP/Huels (now Evonik)) employs a nickel containing catalyst on a silica/aluminium oxide support. See *Make plasticizer olefins via n-butene dimerization* R. H, Friedlander et al., Hydrocarbon Processing, February 1986, pages 31-33, and U.S. Pat. No. 5,177,282. Amorphous silica aluminium oxide supports are useful and commonly utilized. Solid acid catalysts may be optionally practiced with promoters such as $TaF_5$.

In another embodiment, olefin oligomerization can take place in the presence of a homogenous catalyst. Non-limiting examples of such catalysts are provided as follows. The IFP (now Axens) DIMERSOL® processes employs a Ni-based homogeneous catalyst. (Y. Chauvin et al. Chemistry and Industry, 1974, 373-378). U.S. Pat. No. 4,225,743 discloses a homogeneous catalyst system suitable for olefin oligomerization, consisting of a Nickel (II) salt of octanoic acid, ethylaluminium dichloride, and a free fatty acid. Preferably, the catalyst is selected from catalysts comprising a zeolite, nickel oxide or phosphoric acid.

The term "zeolites" is often used to describe the aluminosilicate members of the family of microporous solids known as "molecular sieves". The term molecular sieve refers to a particular property of these materials, i.e., the ability to selectively sort molecules based primarily on a size exclusion process. This is due to a very regular pore structure of molecular dimensions. The maximum size of the molecular or ionic species that can enter the pores of a zeolite is controlled by the dimensions of the channels. These are conventionally defined by the ring size of the aperture, where, for example, the term "8-ring" refers to a closed loop that is built from 8 tetrahedrally coordinated silicon or aluminum atoms and 8 oxygen atoms. These rings are not always perfectly symmetrical due to a variety of effects, including strain induced by the bonding between units that are needed to produce the overall structure, or coordination of some of the oxygen atoms of the rings to cations within the structure. Therefore, the pores in many zeolites may not be cylindrical.

In an embodiment, the at least one zeolite catalyst may include a medium pore size molecular sieve having a Constraint Index of about 1 to about 12. Constraint Index and a method of its determination are described in, for example, U.S. Pat. No. 4,016,218.

Examples of the at least one zeolite catalyst include those of the TON framework type (for example, ZSM-22, ISI-1, Theta-1, Nu-10, and KZ-2), those of the MTT framework type (for example, ZSM-23 and KZ-1), those of the MFI framework type (for example, ZSM-5), those of the MFS framework type (for example, ZSM-57), those of the MEL framework type (for example, ZSM-11), those of the MTW framework type (for example, ZSM-12), those of the EUO framework type (for example, EU-1), those of the AEL framework type (for example, SAPO-11), members of the ferrierite family (for example, ZSM-35) and members of the ZSM-48 family of molecular sieves (for example, ZSM-48). Other examples include zeolites of the MWW family (e.g., MCM-22, MCM-48), zeolites of the MOR framework type, or zeolite beta. As used herein, the term "structure type" is used as described in the Structure Type Atlas, Zeolites 17, 1996.

Preferably, the zeolite is selected from at least one of zeolites having the TON framework type, for example ZSM-22, ZSM-5, ZSM-11, ZSM-12, ZSM-18, ZSM-22, ZSM-23, ZSM-35, ZSM-38, ZSM-48, ZSM-50, zeolites of the MFS framework type, for example ZSM-57, and mixtures thereof.

Mixtures of two or more of zeolites may be used in the oligomerization process. For example, the mixture may include ZSM-22 and ZSM-57 or ZSM-22 and ZSM-5 or ZSM-57 and ZSM-5. The at least one zeolite catalyst may also be combined with other types of catalysts such as a solid phosphoric acid (sPa) catalyst.

The zeolite used in the oligomerization catalyst may have an average crystallite or particle size of up to 15 μm, such as within the range of from 0.01 to 6 μm, alternatively, from 0.05 to 5 μm, and alternatively, from 0.1 to 3 μm. As used herein, "average particle size" refers to the arithmetic average of the diameter distribution of the crystals on a volume basis.

Preferably, the zeolite is used in its proton, or acidic form. To obtain this form, an as-synthesized molecular sieve that has been obtained in an alkaline or alkaline-metal form is advantageously converted to its acid form, for example, by acid treatment, e.g., by HCl, acetic acid, etc. or by ion exchange, for example, ammonium ion exchange. Subsequently, it may undergo calcination before use. The calcined materials may be post-treated, such as by steaming.

The at least one zeolite catalyst may be produced by any suitable method known for the given type of zeolite. One technique includes heating a reaction mixture containing a source of silicon oxide, a source of aluminum oxide and, if appropriate, an organic promoter, for example, a nitrogen or phosphorus-containing organic base, together optionally, with an alkali metal base, and separating the porous aluminosilicate crystals (zeolite precursor crystals) formed. The precursor crystals are then calcined in air or oxygen at a temperature exceeding or about 500° C., for example, at a temperature of 550° C. for about 10 to about 20 hours. As recognized in the art, calcination temperatures and durations may vary depending on the type of zeolite catalyst or combination of zeolite catalysts selected. In one embodiment, the calcined material is exchanged with ammonium ions ($NH_4$+) and subjected to conditions under which the ammonium ions decompose, with the formation of ammonia and a proton, thus, producing an acidic form of the at least one zeolite catalyst. Alternatively, the acidic form of the catalyst may be obtained by acid exchange with hydrochloric acid, acetic acid, etc. If desired, however, the calcined material may be used as a catalyst without first being exchanged with ammonium ions, since the material already possesses acidic sites.

Ammonium exchanged and calcined monodimensional 10-rings zeolites (e.g., ZSM-22 and ZSM-23) may be treated to selectivate their surface, thereby, forming a selectivated catalyst. This selectivation may be achieved in numerous ways. In an embodiment, the at least one zeolite catalyst may be titrated with an organic nitrogen base, such as collidine. See, for example, U.S. Pat. No. 5,026,933. Another example is by depositing a crystalline Si:Al layer on a core of zeolite where this layer has a higher Si:Al ratio than the untreated zeolite. See, for example, U.S. Pat. No. 6,013,851.

Although much of the discussion above is directed to aluminosilicate zeolites, it is possible to use material in which silicon and aluminum have been replaced in whole or in part by other elements, for example, any one or more of a Group 2 to Group 15 atom. For example, silicon may be replaced by or contacted with germanium and aluminum or may be replaced with boron, gallium, chromium, and iron. As used herein, these materials containing such replacement lattice elements may also be termed zeolites.

It may be desirable to incorporate the molecular sieves or zeolites mentioned above with another material that is resistant to the temperatures and other conditions employed in the olefin oligomerization process. Thus the molecular sieves or zeolites may be used in the form of an extrudate with binder, where the molecular sieve or zeolite is dispersed within a conventional binder. Binding is typically done by forming a pill, sphere, or extrudate. The extrudate is usually formed by extruding the molecular sieve, optionally in the presence of a binder, and drying and calcining the resulting extrudate. The binder materials used are resistant to the temperatures and other conditions, e.g., mechanical attrition, which occur in various hydrocarbon conversion processes.

Examples of binder materials that may be employed with the molecular sieves or zeolites suitable for use in the process of the invention include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Naturally occurring clays which may be used include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or after being subjected to calcination, acid treatment or chemical modification.

Examples of other materials include porous matrix materials such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Exemplary catalyst materials and processes for making such catalysts may also be found in U.S. Pat. Nos. 3,960,978, 4,016,218, 4,021,502, 4,381,255, 4,560,536, 4,919,896, 5,446,222, 5,672,800, 6,143,942, 6,517,807, 6,884,914, U.S. Patent Application Publication No. 2006/0199987, EP 746 538 A, WO 1994/12452 WO 2005/118512, WO 2005/118513, WO 2007/006398, and WO 2008/088452. See also "Atlas of Zeolite Structure Types," Eds. W. H. Meier, D. H. Olson and Ch. Baerlocher, Elsevier, Fourth Edition, 1996.

According to the present invention, the olefin feed with reduced level of acetonitrile is contacted with a catalyst under conditions suitable to oligomerize the olefins. The olefin oligomerization reaction system may include one or more of a fixed bed reactor, a packed bed reactor, a tubular reactor, a fluidized bed reactor, a slurry reactor, a continuous catalyst regeneration reactor, and any combination thereof. These reactors may be operated in any combination such as, for example, in series and/or parallel sequence. In several embodiments, they may be operated in semi-continuous (i.e., continuous but down for routine maintenance), continuous, or batch mode.

The oligomerization conditions may temperatures from about 80° C. to about 350° C. Close to and above the upper end of the range, deoligomerization rates increase and may predominate over the oligomerization reaction providing an upper limit to practical operation. More typically, the reaction temperature is from about 130° C. to about 320° C., preferably from about 135° C. to about 310° C., and even more preferably from about 160° C. to about 270° C.

The pressure may be in the range of from about 400 psig to about 4000 psig (2860 to 27688 kPa), and alternatively, from about 500 psig to about 1500 psig (3550 to 10446 kPa).

The olefin weight hourly space velocity based on catalyst, may be in the range of from about 0.1 $hr^{-1}$ to about 20 $hr^{-1}$ or from about 0.5 $hr^{-1}$ to about 5 $hr^{-1}$.

In one embodiment, process is conducted at a temperature of 80-350° C.; an olefin weight hourly space velocity of 0.1-20 $hr^{-1}$; and a pressure of 2860-27688 kPa.

In another embodiment, the process is conducted at a temperature of 130-320° C.; an olefin weight hourly space velocity of 0.5-5 $hr^{-1}$; and a pressure of 3550-10446 kPa.

In a class of embodiments, the oligomers formed in the olefin oligomerization step of the process of the invention may include a hydrocarbon composition comprising at least 80 wt %, alternatively, at least 90 wt % based upon the total weight of the reactor effluent (the final reactor effluent if one or more reactors are utilized) of $C_6$ to $C_{20+}$ olefin or a mixture thereof.

The oligomer (higher olefin) product is useful in many applications and is the starting material for further conversion processes. For example, the oligomer product may be polymerized to produce polyolefins that have application in the plastic industry or polymerized to form synthetic basestocks for lubricants. The oligomer product may undergo hydroformylation and subsequently hydrogenation to produce alcohols. The alcohols may be used in industry such as, for example, solvents, or be incorporated into the production of detergents/surfactants. The alcohols may further be used in many other areas of industry such as, for example, undergoing esterification to produce esters that have application as plasticizers. The oligomer product may also be a blend component for fuels.

The present invention will now be demonstrated by way of example only.

EXAMPLES

In these examples, several guard bed materials, placed upstream of an olefin oligomerization catalyst, were tested in a fixed bed reactor by comparing the time on stream needed to reach 50% of the initial activity of the oligomerization catalyst with an olefin feed contaminated with acetonitrile.

Guard Beds

Gamma aluminium oxide was obtained by thermal treatment of different boehmites. No additives were used other than water to make a slurry or a paste.

The materials were prepared by combining and mixing at room temperature a suitable amount of pseudoboehmite aluminium oxide hydrate corresponding to 2.0 parts of $Al_2O_3$ with 35 parts of de-ionised (DI) water. The mixture was stirred for about 4 hours at room temperature to form uniform slurry; the resultant slurry was centrifuged for removal of the supernatant (without additional washing). The obtained solid was dried overnight at 80° C. in air and calcined at 540° C. (Examples 1, 3, 4, 6, 8) or 650° C. (Examples 1, 7, 9) for 4 hours in air, then ground to make a uniform powder, then pressed and sized, for use as the guard bed material. By the thermal treatment the pseudo-boehmite was transformed to gamma aluminium oxide.

The specific surface area was determined by nitrogen adsorption at 77° K and is listed in $m^2/g$ in Table 1. The morphology and largest crystal dimension were determined based on Scanning Electron Micrographs of 30 crystals for each sample. The micrographs were taken with a JEOL JSM-6340F Field-Emission-Gun scanning electron microscope operated at 2 kV and 12 mA. Prior to measurement, samples were dispersed in ethanol, subjected to 5 to 30 minutes ultrasonic treatment, deposited on SEM sample holders and dried at room temperature.

A morphology described as thin platelet means that the crystals had flattened shapes such as flat hexagonal prisms, with the ratio of the height, defined as A, to the largest dimension (width) of the cross-section, defined as B, A/B of smaller than 0.5. In case of a thick block the A/B ratio was larger than 0.5.

TABLE 1

Guard bed materials

| Example | Raw Material | Boehmite Morphology | Largest dimension [nm] | Temp [° C.] | BET [$m^2/g$] |
|---|---|---|---|---|---|
| 1 | Versal 200[(1)] | Needle | 3 | 540 | 302 |
| 2 | Versal 200[(1)] | Needle | 3 | 650 | 246 |
| 3 | Versal 300[(1)] | Needle | 3 | 540 | 275 |
| 4 | Versal 700[(1)] | Needle | 3 | 540 | 251 |
| 5 | Pural SB[(2)] | Thin Platelets | 5 | 540 | 250 |
| 6 | Pural TH60[(2)] | Thick Blocks | 6 | 540 | 220 |
| 7 | Pural TH60[(2)] | Thick Blocks | 6 | 650 | 174 |
| 8 | Pural TH100[(2)] | Thick Blocks | 10 | 540 | 170 |
| 9 | Pural TH100[(2)] | Thick Blocks | 10 | 650 | 137 |

[(1)]Available from UOP
[(2)]Available from Sasol

Table 1 shows that gamma alumina obtained from Versal boehmite had a higher surface area than those made from the Pural boehmites. The Versal boehmite had a primary crystal size of 3 nm with needle type morphology. Upon heat-treatment at 540° C., gamma aluminium oxide with high surface area was formed. At higher temperatures the surface area gradually decreased and the surface properties were further modified by dehydration of the structure.

The crystallites of Pural TH60 were 6 nm and those of Pural TH100 on average 10 nm. Both were thick blocks. Keeping all other parameters the same, the surface area was typically lower for boehmite materials treated at higher temperature, a trend which was observed irrespective of the morphology of the crystals of the starting materials.

Olefin Oligomerization Catalyst

The oligomerization catalyst used was ExxonMobil commercially available catalyst of alumina (25%) bound ZSM-22 (with $Si/Al_2$=65) (75%). Extrudates were crushed and sieved to 0.3-0.6 mm.

General Testing Procedure

All experiments were carried out in fixed bed reactors (FBR) in upflow mode. The reactor was 260 mm long and had an internal diameter of 7 mm. Inside the reactor was a 1/16" tube with a duplex thermocouple. Each reactor was loaded with fixed volumes for inert material SiC (40 vol %), guard bed (5 vol %) and catalyst (55 vol %). 100 mg guard bed (40/60 vol % guard bed/SiC) and 500 mg of catalyst (15/85 vol % catalyst/SiC) were loaded (dry weights). The SiC used was 120 mesh (0.125 mm) Guard bed and catalysts were sized between 0.3 and 0.6 mm before loading. The catalysts and guard bed materials were loaded at ambient conditions in the FBR. Prior to start-up, the guard beds and catalysts in the reactors were pretreated as specified in Table 3.

TABLE 2

Guard bed and catalyst treatment prior to start-up

| Step # | Temperature (° C.) | Time (h) | Comment |
|---|---|---|---|
| 1 | 80 | 0.5 | Nitrogen flow |
| 2 | 120 | 1.0 | Nitrogen flow |
| 3 | 170 | 0.5 | Nitrogen flow |

The feed was a spiked synthetic mixture of propane (diluent), propene and isobutane (internal standard), all supplied by l'Air Liquide. The feed composition is shown in Table 3.

TABLE 3

Feed composition

| Component | Weight |
|---|---|
| Propene | 50% |
| Propane | 40% |
| Isobutane | 10% |
| Water | 100 ppm |
| Acetonitrile | 1 ppm |

The guard beds were all tested under the same conditions: feed flow rate of 10 g/h, reactor temperature of 220° C. and pressure of 7000 kPa.

Results

The conversion of propylene was followed as a function of time on stream (TOS, expressed in hours) and the time to reach 50% conversion was determined for all examples. The conversion is determined by measuring the actual composition of the feed and product samples using on-line gas chromatography. The 10% isobutane in the feed is an Internal Standard and the relative disappearance of the propene versus the Internal Standard is used to calculate the conversion in the product samples. The gas chromatograph uses a HP-1MS column (30 m, 0.25 mm, 1.0 μm) to trap any heavies greater than C6 from the product and a HP-PLOT AL2O3 KCL column (30 m, 0.25 mm, 5 μm) to elute the light components to a flame ionization detector. The time to reach 50% conversion was compared to the value obtained for reference Example 3 and the difference between TOS for the sample tested and TOS for reference example 3 was expressed as delta TOS (hr). Positive values of delta TOS are thus obtained for guard bed materials that are more efficient in protecting the oligomerization catalyst from acetonitrile contamination than reference example 3, and negative delta TOS are obtained for guard bed materials that are more efficient in protecting the oligomerization catalyst from acetonitrile contamination than reference example 3.

The results are shown in Table 4.

TABLE 4

| Example | Raw Material | Morphology | Largest dimension of Boehmite [nm] | Temp [° C.] | $T_x$ [hr] | $T_x - T_{ref}$ [hr] | BET [$m^2/g$] |
|---|---|---|---|---|---|---|---|
| 1 | Versal 200 | Needle | 3 | 540 | 46 | 4 | 302 |
| 2 | Versal 200 | Needle | 3 | 650 | 42 | 0 | 246 |
| 3 [Reference] | Versal 300 | Needle | 3 | 540 | 42 | 0 | 275 |
| 4 | Versal 700 | Needle | 3 | 540 | 42 | 0 | 251 |
| 5 | Pural SB | Thin Platelets | 5 | 540 | 39 | −3 | 250 |
| 6 | Pural TH60 | Thick Blocks | 6 | 540 | 38 | −4 | 220 |
| 7 | Pural TH60 | Thick Blocks | 6 | 650 | 33 | −9 | 174 |
| 8 | Pural TH100 | Thick Blocks | 10 | 540 | 34 | −8 | 170 |
| 9 | Pural TH100 | Thick Blocks | 10 | 650 | 30 | −12 | 137 |

These examples show that oligomerization occurs more efficiently using gamma aluminium oxide guard beds prepared from needle shaped boehmite, compared to gamma aluminium oxide obtained from other sources.

Materials prepared from boehmite with needle morphology were of small particle size, had higher surface area and were preferred as guard bed material above those made from larger particles and platelet morphology. The latter typically had smaller surface area when prepared under the same conditions. Without wishing to be bound by any theory, it is believed that gamma alumina made from larger particles and with platelet morphology results in reduced availability of active surface sites and therefore reduced nitrile removal capacity.

The invention claimed is:

1. An olefin oligomerization process comprising the steps of:

i) reducing the level of nitriles in an olefin feed by contacting the feed with a guard bed comprising gamma alumina having a surface area greater than 250 $m^2/g$; and ii) contacting the olefin feed obtained in step i) with an oligomerization catalyst under conditions suitable to oligomerize the olefins in the feed wherein a process for preparing the gamma alumina comprises sintering needle shaped boehmite, wherein the largest dimension of the needle shaped boehmite is 3 nm or less.

2. The process according to claim 1, wherein the guard bed comprises at least another metal oxide besides gamma alumina.

3. The process according to claim 2, wherein the other metal oxide is selected from the group consisting of tin oxide, zirconium oxide, titanium oxide, iron oxide, tungsten oxide and alumina of any phase other than gamma alumina, and mixtures thereof.

4. The process according to claim 1, wherein the nitriles are selected from the group consisting of acetonitrile, propionitrile and mixtures thereof.

5. The process according to claim 1, wherein the oligomerization catalyst used in step (ii) is selected from the group consisting of zeolite, nickel oxide, phosphoric acid, mixtures or combinations thereof.

6. The process according to claim 1, wherein the guard bed used in step i) and the oligomerization catalyst used in step ii) are in separate vessels.

7. The process according to claim 1, wherein the temperature employed during process step i) is in the range of 150 to 250° C.

8. The process according to claim 1, wherein the olefin is selected from olefins having 3 to 6 carbon atoms.

* * * * *